United States Patent [19]

Toyofuku et al.

[11] Patent Number: 5,356,916
[45] Date of Patent: Oct. 18, 1994

[54] 1,2,4-OXADIAZOLE DERIVATIVES HAVING MONOAMINE OXIDASE B ENZYME-INHIBITORY ACTIVITY

[75] Inventors: Hatsunori Toyofuku, Yokohama; Jun Matsumoto, Kanagawa; Toshie Takahashi, Yamato; Masakazu Ebie, Gifu; Naomi Sasada, Isehara; Mitsuzi Agata; Shohei Sawaki, both of Kanagawa; Masayoshi Goto, Isehara, all of Japan

[73] Assignee: Wakamoto Pharmaceutical Co., Ltd., Tokyo, Japan

[21] Appl. No.: 830,298

[22] Filed: Jan. 31, 1992

[30] Foreign Application Priority Data

Mar. 22, 1991 [JP] Japan .................................. 3-081198

[51] Int. Cl.$^5$ .................... C07D 271/06; A61K 31/41
[52] U.S. Cl. .................................. 514/364; 514/340; 544/138; 544/367; 546/209; 546/277; 548/131
[58] Field of Search ..................... 548/131; 546/277; 514/364, 340

[56] References Cited

U.S. PATENT DOCUMENTS

| | | | |
|---|---|---|---|
| 3,697,530 | 10/1972 | Imai et al. | 260/295 |
| 3,887,573 | 6/1975 | Breuer et al. | 514/364 |
| 4,764,522 | 8/1988 | Imhof et al. | 514/354 |
| 4,871,753 | 10/1989 | Rohr | 514/364 |
| 4,929,628 | 5/1990 | McArthur et al. | 514/364 |
| 5,100,910 | 3/1992 | Milcent et al. | 514/364 |
| 5,175,177 | 12/1992 | Diana | 514/364 |
| 5,175,178 | 12/1992 | Diana | 514/364 |

FOREIGN PATENT DOCUMENTS

| | | |
|---|---|---|
| 276432 | 8/1988 | European Pat. Off. . |
| 348257 | 12/1989 | European Pat. Off. . |
| 45-21833 | 7/1970 | Japan . |
| 45-21834 | 7/1970 | Japan . |
| 47-7373 | 3/1972 | Japan . |
| 47-7374 | 3/1972 | Japan . |
| 51-143669 | 12/1976 | Japan . |
| 54-41594 | 12/1979 | Japan . |
| 61-60657 | 3/1986 | Japan . |
| 63-162680 | 7/1988 | Japan . |
| 1-216981 | 8/1989 | Japan . |
| 2-56471 | 2/1990 | Japan . |
| 1341222 | 4/1970 | United Kingdom . |

OTHER PUBLICATIONS

*Tetrahedron*, vol. 46 (5), pp. 1659–1668, 1990 to Belen'-kii et al.
*J. Organic Chem.*, vol. 30 (12), pp. 4359–4361 to Durden et al. (1965).
*Chem. Abst.*, vol. 57 (4), Abstract No. 4650h (1962).
*Artherosclerosis*, vol. 17, pp. 121–129 to Imai et al. (1973).

(List continued on next page.)

*Primary Examiner*—Robert Gerstl
*Attorney, Agent, or Firm*—Burns, Doane, Swecker & Mathis

[57] ABSTRACT

A 1,2,4-oxadiazole derivative is represented by the following general formula (I):

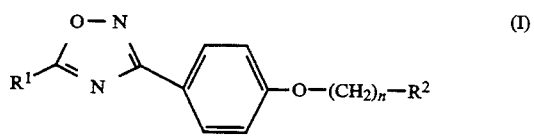

wherein $R^1$ represents a lower alkyl or cycloalkyl group, a lower alkyl group substituted with a halogen atom, a lower alkylamino group or a phenyl group; $R^2$ represents a hydrogen atom, a lower dialkylamino group, a cyclic alkylamino group, a cyclic amino group having an oxygen or nitrogen atom in the ring, a phenyl group which may be substituted with a halogen atom, a pyridyl group, an imidazolyl group, an alkylimidazolyl group, a benzimidazolyl group or a 2-oxopyrrolidinyl group; and n is 1, 2 or 3. The derivative has excellent monoamine oxidase-inhibitory activity and is effective as a medicine for treating Parkinson's disease.

13 Claims, No Drawings

OTHER PUBLICATIONS

*J. Heterocyclic Chemistry*, vol. 16, pp. 1469–1475 to Palazzo et al. (1979).
*J. Medicinal and Pharmaceutical Chemistry*, vol. 4 (2), pp. 351–367 (1961).
S. Yurugi et al., *Chem. Pharm. Bull.*, 21(8), pp. 1641–1650, (1973).
S. Yurugi et al., *Chem. Pharm. Bull.*, 21(9), pp. 1885–1893 (1973).
*Chemical Abstracts*, vol. 113, 113:172052m, p. 711 (1990).
*Chemical Astracts*, vol. 112, 112:93950d, p. 307, (1990).
*Chemical Abstracts*, vol. 113, 113:191331t, p. 723, (1990).
Guy D. Diana et al., *J. Med. Chem.*, 31, pp. 540–544, (1988).
P. J. Sanfilippo et al., *J. Med. Chem.*, 31, pp. 1778–1785, (1988).
*Chemical Abstracts*, vol. 110, 110:75518y, p. 655, (1989).
*Chemical Abstracts*, vol. 105, 105:97323e, p. 621, (1986).
*Chemical Abstracts*, vol. 75, 118320f, p. 221, (1971).

1,2,4-OXADIAZOLE DERIVATIVES HAVING MONOAMINE OXIDASE B ENZYME-INHIBITORY ACTIVITY

BACKGROUND OF THE INVENTION

The present invention relates to a 1,2,4-oxadiazole derivative which can inhibit monoamine oxidase B (hereinafter referred to as "MAO-B") and a method for preparing the derivative.

It has been believed that about a hundred of thousand persons presently suffer from Parkinson's disease in the country and the onset thereof is in general observed in aged persons of 50-year-old or higher. The population of the aged would be more and more increased in the future and thus there has been a strong need for the development of medicines effective for treating Parkinson's disease.

It has been considered that Parkinson's disease is caused due to the reduction in the ability of producing dopamine which is essential and indispensable as a neurotransmitter in the brain when one suffers from nigrostriatal disorder in the basal nucleus region of the brain. Presently, there has commonly been administered L-dopa as a precursor of dopamine for treating Parkinson's disease. The administration of an MAO-B inhibitor permits a significant extension of the residence time of dopamine formed through the metabolism of the L-dopa in the brain and thus can enhance the efficacy thereof. Moreover, it would further allow the reduction of dose of the L-dopa and, therefore, it likewise serves to substantially relieve side-effects of the L-dopa such as nausea, arhythmia, orthostatic hypotension and symptoms of depression.

There have been investigated the MAO-B inhibitors on the basis of these basic assumptions and d,l-Deprenil has first been developed as a medicine for the treatment of Parkinson's disease among other compounds. The effectiveness of this compound has clinically been proved in the United States and Europe and it has been practically used as a medicine for treating this disease.

SUMMARY OF THE INVENTION

Accordingly, an object of the present invention is to provide a novel compound having MAO-B inhibitory activity.

Another object of the present invention is to provide a method for preparing such a compound.

A further object of the present invention is to provide a monoamine oxidase B-inhibitory composition containing the foregoing 1,2,4-oxadiazole derivative.

The inventors of this invention have conducted various studies to develop novel compounds effective for the treatment of Parkinson's disease other than d,l -Deprenil, have found out that specific derivatives of 1,2,4-oxadiazole exhibit an effect of inhibiting MAO-B in high selectivity and are effective for the treatment of Parkinson's disease and thus have completed the present invention.

According to an aspect of the present invention, there is provided a 1,2,4-oxadiazole derivative represented by the following general formula (I) as well as an acid addition salt thereof:

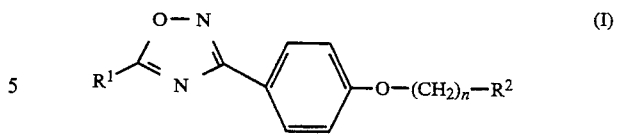

wherein $R^1$ represents a lower alkyl or cycloalkyl group, a lower alkyl group substituted with a halogen atom, a lower alkylamino group or a phenyl group; $R^2$ represents a hydrogen atom, a lower dialkylamino group, a cyclic alkylamino group, a cyclic amino group having an oxygen or nitrogen atom in the ring, a phenyl group which may be substituted with a halogen atom, a pyridyl group, an imidazolyl group, an alkyl imidazolyl group, a benzimidazolyl group or a 2-oxopyrrodinyl group; and n is 1, 2 or 3.

Among the compounds represented by Formula (I) and acid addition salts thereof, preferred are pharmaceutically acceptable salts and examples thereof include salts with inorganic acids such as hydrochlorides, hydrobromides, hydroiodides, sulfates and phosphates; and salts with organic acids such as oxalates, maleates, fumarates, lactates, malates, citrates, tartarates, benzoates and methanesulfonates. The compounds of Formula (I) may also be present in the form of hydrates and, therefore, these hydrates are likewise included in the scope of the present invention.

According to another aspect of the present invention, there is provided a method for preparing the 1,2,4-oxadiazole derivative of Formula (I) which comprises the steps of reacting an amidoxime derivative represented by the following general formula (II):

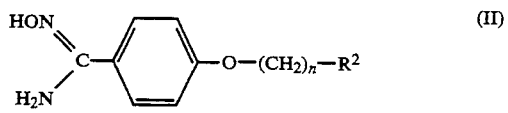

(wherein $R^2$ represents a hydrogen atom, a lower dialkylamino group, a cyclic alkylamino group, a cyclic amino group having an oxygen or nitrogen atom in the ring, a phenyl group which may be substituted with a halogen atom, a pyridyl group, an imidazolyl group, an alkyl imidazolyl group, a benzimidazolyl group or a 2-oxopyrrodinyl group; and n is 1, 2 or 3) with a corresponding acyl halide or acid anhydride in the presence of a base in a solvent and then isolating the reaction product.

DESCRIPTION OF THE PREFERRED EMBODIMENTS

The present invention will be explained in more detail below.

The terms used herein will be detailed below. First, the term "lower" means that each corresponding group has 1 to 5 carbon atoms unless otherwise specified. Therefore, the lower alkyl groups may be linear or branched ones having 1 to 5 carbon atoms. Specific examples thereof are methyl, ethyl, propyl and isopropyl groups. The term "lower alkyl group substituted with a halogen atom" means lower alkyl groups which are substituted with 3 to 7 halogen atoms such as chlorine and fluorine atoms and specific examples thereof include trichloromethyl, trifluoromethyl, pentafluoroethyl and heptafluoropropyl groups.

The term "cyclic alkylamino group" means an alicyclic alkylamino group. Specific examples thereof are piperidino group.

The term "cyclic amino group having an oxygen or nitrogen atom in the ring" stands for a cyclic compound which is an alicyclic alkylamino group having an oxygen or nitrogen atom in the ring and specific examples thereof are morpholino and piperazino groups.

The compounds of the present invention represented by Formula (I) can be prepared according to the methods represented by the following reaction scheme:

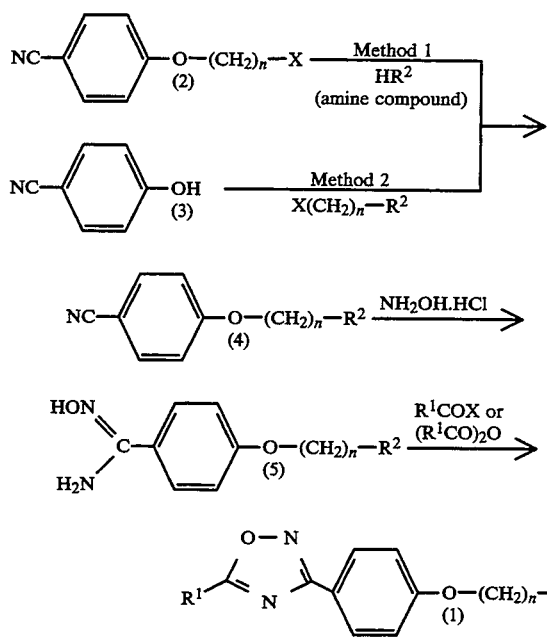

In the foregoing formulae, $R^1$ and $R^2$ are the same as those defined above in connection with Formula (I) and X represents a halogen atom.

As will be seen from the foregoing reaction scheme, benzonitrile derivatives (4) can be prepared according to the following methods 1 or 2 which may arbitrarily be selected.

If they are prepared according to the method 1, the benzonitrile derivative can be prepared by reacting 4-(ω-haloalkoxy)benzonitrile (2) with an amine compound ($HR^2$) in an amount of 1 to 10 times the equivalent amount of the compound (2) in the presence or absence of an appropriate solvent and a base at a temperature ranging from room temperature to 120° C. for 1 to 24 hours. In this case, the amine as a reagent may also serve as a solvent or a base. Examples of proper solvents are pyridine, N,N-dimethylformaminde, dimethysulfoxide, N-methylmorpholine, toluene, tetrahydrofuran, ethanol and propanol. In addition, examples of bases include anhydrous potassium carbonate, sodium alkoxide, potassium tertiary butoxide, sodium hydride, sodium hydroxide and potassium hydroxide.

For example, the following benzonitrile derivatives can be prepared by the method 1:

4-[3-(1H-imidazol-1-yl)propoxy]benzonitrile, 4-[2-(1H-imidazol-1-yl)ethoxy]benzonitrile, 4-[3-(1H-2-methylimidazol-1-yl) propoxy]benzonitrile, 4-[3-(1H-benzimidazol-1-yl)propoxy]benzonitrile, 4-(3-diethylaminopropoxy)benzonitrile, 4-(3dipropylaminopropoxy)benzonitrile, 4-[3-(4-methylpiperazinyl)-propoxy]benzonitrile, 4-(3-morpholinopropoxy)benzonitrile and 4-[3-(2-oxopyrrolidinyl)propoxy]benzonitrile.

According to the method 2, the benzonitrile derivative can be prepared by reacting 4-cyanophenol (3) with an alkyl halide [$X-(CH_2)_n—R^2$] in an amount of 1 to 3 times the equivalent amount of the compound (3) at a temperature ranging from room temperature to 120° C. for 1 to 24 hours in the presence of a base in a solvent. The solvent and base used herein are the same as those defined above in connection with the method 1.

For instance, the following benzonitrile derivatives can be prepared by the method 2:

4-(3-phthalimidopropoxy)benzonitrile, 4-(3-piperidinopropoxy) benzonitrile, 4-[3-(3-pyridyl)-propoxy]benzonitrile, 4-(3-phenylpropoxy)benzonitrile, 4-propoxybenzonitrile, 4-benzyloxybenzonitrile, 4-(3-pyridylmethyl)benzonitrile, 4-(4-pyridylmethyl) benzonitrile and 4-(3-chlorobenzyloxy)benzonitrile.

The resulting benzonitrile derivative (4) is dissolved in a mixed solvent comprising a proper alcohol and water together with 1 to 5 eq. of hydroxylamine hydrochloride, followed by addition of 0.5 eq. of a base such as sodium carbonate or potassium carbonate and reaction at a temperature ranging from room temperature to the reflux temperature of the solvent to give an amidoxime derivative (5) (corresponding to the foregoing general formula (II)). Examples of proper alcohols are methanol, ethanol and n-propanol.

The amidoxime derivatives (5) which can be prepared in the foregoing method are, for instance, the following compounds:

4-[3-(1H-imidazol-1-yl)propoxy]benzamidoxime, 4-[2-(1H-imidazol-1-yl)ethoxy]benzamidoxime, 4-[3-(1H-2-methylimidazol-1-yl) propoxy]benzamidoxime, 4-[3-(1H-benzimidazol-1-yl)propoxy]benzamidoxime, 4-(3-diethylaminopropoxy)benzamidoxime, 4-(3-dipropylaminopropoxy)benzamidoxime, 4-[3-(4-methylpiperazinyl)propoxy]benzamidoxime, 4-(3-morpholinopropoxy)benzamidoxime, 4-[3-(2-oxopyrrolidinyl)propoxy]benzamidoxime, 4-(3-phthalimidopropoxy) benzamidoxime, 4-(3-piperidinopropoxy)benzamidoxime, 4-[3-(3-pyridyl) propoxy]benzamidoxime, 4-(3-phenylpropoxy)benzamidoxime, 4-propoxybenzamidoxime, 4-benzyloxybenzamidoxime, 4-(3-pyridylmethyl) benzamidoxime, 4-(4-pyridylmethyl)benzamidoxime and 4-(3-chlorobenzyloxy)benzamidoxime.

Then the compounds of Formula (I) can easily be synthesized by reacting the foregoing amidoxime derivative (5) with an acyl halide or acid anhydride having a group corresponding to $R^1$ of Formula (I), in an amount of 1 to 5 times the molar amount of the compound (5) in a solvent (provided that if the solvent is neutral, in the presence of a proper base), at a temperature ranging from 0° to 150° C. for 3 to 30 hours.

Typical examples of solvents used in this reaction include pyridine, dioxane, toluene and benzene. Moreover, examples of proper bases are N-methylmorpholine, triethylamine, sodium hydroxide, potassium hydroxide and pyridine.

The compounds of Formula (I) thus prepared are in the form of crystalline or oily substances and thus can optionally be subjected to column chromatography or recrystallization to give highly pure products.

Acid-addition salts of the compounds of Formula (I) can likewise easily be obtained by treating the compounds with a physiologically acceptable acid, for instance, an inorganic acid such as hydrochloric acid, hydrobromic acid, hydriodic acid, sulfuric acid or phosphoric acid; or an organic acid such as oxalic acid, maleic acid, fumaric acid, lactic acid, malic acid, citric acid, tartaric acid, benzoic acid or methanesulfonic acid in the usual manner.

The compounds of the present invention can be administered through either oral or parenteral routes (such as subcutaneous, intravenous, nazal, eye dropping and intrarectal routes) in the usual manner.

The amount of the effective component to be administered is not critical and can be varied over a wide range. It is a matter of course that it can be adapted for each specific case so as to satisfy specific requirements, but desirably ranges from 0.1 mg to 1000 mg/day expressed in terms of the amount of the compound in its free state.

The compounds of the present invention can be shaped in any dosage form according to methods known per se, such as tablets, film coated tablets, soft and hard capsules, powders, granules, sugar coated pills, suppositories, solutions, emulsions, suspensions, injections, eye drops and eye ointments. Moreover, these pharmaceutical preparations may further comprise other substances having therapeutic activities.

The present invention will hereinafter be explained in more detail with reference to the following non-limitative working Examples, Examples of Pharmaceutical Preparations and Reference Examples.

Pharmaceutical Preparation 1 (tablet)

A tablet was prepared in the usual manner, which comprised 40 mg of the compound of Example 2, 120 mg of corn starch, 13.5 mg of gelatin, 45 mg of lactose, 6.75 mg of potato starch and 2.25 mg of Aerosil (registered trade mark).

Pharmaceutical Preparation 2 (tablet)

A tablet was prepared in the usual manner, which comprised 20 mg of the compound of Example 22, 26 mg of corn starch, 90 mg of lactose, 0.5 mg of magnesium stearate, 1.5 mg of talc and 2.5 mg of hydroxypropyl cellulose.

Pharmaceutical Preparation 3 (gelatin hard capsule)

A gelatin hard capsule was prepared in the usual manner, which comprised 10 mg of the compound of Example 21, 140 mg of lactose, 96.35 mg of corn starch, 2.4 mg of talc and 1.25 mg of magnesium stearate.

Reference Example 1 (Method 1)

To 30 ml of n-propanol, there were added 2.695 g of 4-(3-chloropropoxy)benzonitrile and 10.21 g of imidazole and the resulting mixture was heated under reflux for 24 hours. After concentration of the reaction mixture, water was added to the residue obtained, followed by extraction with chloroform, washing of the resulting extract with water and then drying the same. After concentration of the extract, the residue obtained was recrystallized from a mixture of ether and n-hexane, followed by addition of n-hexane, filtration and drying to give 2.575 g (yield 75.3%) of 4-[3-(1H-imidazolyl)-propoxy]benzonitrile having a melting point of 60.0°–61.5° C.

Reference Example 2

There were dissolved, in 20 ml of dry N,N-dimethylformamide, 1.797 g of 4-(3-chloropropoxy)benzonitrile, 985 mg of 2-methylimidazole and 1 765 g of a 90% potassium t-butoxide, then the resulting solution was stirred at room temperature for 4.5 hours, poured into ice water, the resulting precipitates were filtered off and washed with water. The precipitates were recrystallized from a mixed solution of ethanol and water to give 1.682 g (yield 69.7%) of 4-[3-(2-methylimidazol-1-yl)propoxy]benzonitrile.

The same procedures used above were repeated to prepare compounds listed in the following Table 1.

TABLE 1

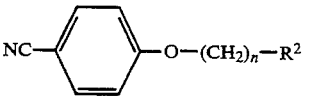

| No. | n | R² |
|---|---|---|
| 1 | 3 |  |
| 2 | 3 | 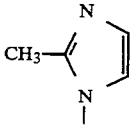 |
| 3 | 3 | 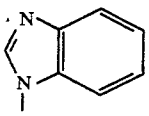 |
| 4 | 3 | —N(C₂H₅)₂ |
| 5 | 3 | —N(CH₂CH₂CH₃)₂ |
| 6 | 3 | 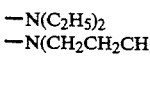 |
| 7 | 3 | 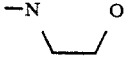 |
| 8 | 3 | 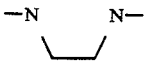 |
| 9 | 2 | 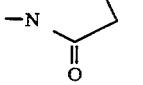 |

Reference Example 3 (Method 2)

There was dissolved 3.574 g of p-cyanophenol in 30 ml of N,N-dimethylformamide, followed by addition of 4.364 g of a 90% potassium t-butoxide and stirring at room temperature for 30 minutes. Then 6.570 g of 1-bromo-3-phenylpropane was dropwise added to the solution and the mixture was stirred for 20 hours. The reaction solution was added to ice water, the resulting precipitates were filtered off, washed with water and recrystallized from a mixture of ethanol and n-hexane to give 5.176 g (yield 72.7%) of 4-(3-phenylpropoxy)benzonitrile.

The same procedures used above were repeated to prepare compounds listed in the following Table 2.

TABLE 2

NC—⟨C6H4⟩—O—(CH2)n—R²

| No. | n | R² |
|---|---|---|
| 1 | 3 | phthalimido (2,3-dihydro-1,3-dioxo-1H-isoindol-2-yl) |
| 2 | 3 | piperidin-1-yl |
| 3 | 3 | pyridin-3-yl |
| 4 | 3 | phenyl |
| 5 | 3 | H |
| 6 | 1 | phenyl |
| 7 | 1 | pyridin-3-yl |
| 8 | 1 | pyridin-4-yl |
| 9 | 1 | 2-chlorophenyl |

Reference Example 4

There was suspended, in 60 ml of ethanol, 9.09 g of 4-]3-(1H-imidazol-1-yl)propoxy]benzonitrile and a solution of 4.17 g of hydroxylamine hydrochloride in 15 ml of water was dropwise added to the suspension. Then 3.18 g of sodium carbonate was added to the suspension followed by heating under reflux with stirring. After 24 hours, the reaction mixture was added to ice water, the resulting precipitates were filtered off, washed with water and then recrystallized from ethanol to give 6.713 g (yield 64.5%) of 4-[3-(1H-imidazol-1-yl) propoxy]benzamidoxime.

The same procedures used above were repeated to prepare compounds listed in the following Table 3.

TABLE 3

(HON)(H2N)C—⟨C6H4⟩—O—(CH2)n—R²

| No. | n | R² |
|---|---|---|
| 1 | 3 | imidazol-1-yl |
| 2 | 3 | 2-methylimidazol-1-yl |
| 3 | 3 | benzimidazol-1-yl |
| 4 | 3 | —N(C2H5)2 |
| 5 | 3 | —N(CH2CH2CH3)2 |
| 6 | 3 | morpholin-4-yl |
| 7 | 3 | 4-methylpiperazin-1-yl |
| 8 | 2 | imidazol-1-yl |
| 9 | 3 | phthalimido |
| 10 | 3 | piperidin-1-yl |
| 11 | 3 | pyridin-3-yl |
| 12 | 3 | phenyl |
| 13 | 3 | H |

TABLE 3-continued

HON\C(—C₆H₄—O—(CH₂)ₙ—R²)/H₂N

| No. | n | R² |
|---|---|---|
| 14 | 1 | phenyl |
| 15 | 1 | 3-pyridyl |
| 16 | 1 | 4-pyridyl |
| 17 | 1 | 2-chlorophenyl |
| 18 | 1 | 2-oxopyrrolidin-1-yl |

EXAMPLE 1

3-[4-[3-(1H-imidazol-1-yl)propoxy]phenyl]-5-ethyl-1,2,4-oxadiazole

There was suspended, in 5 ml of dry pyridine, 521 mg of 4-[3-(1H-imidazol-1-yl)propoxy]benzamidoxime. After gradual and dropwise addition of 194 mg of propionyl chloride and stirring at room temperature for one hour, the suspension was heated to a temperature ranging from 80° to 90° C. for 3.5 hours with stirring. The suspension was added to ice water and the pH thereof was adjusted to 9 to 10 by the addition of potassium carbonate. Then the suspension was extracted with ether and the extract was washed with water and then dried. After concentration of the extract, the resulting residue was purified by silica gel column chromatography (eluent: 98% chloroform-ethanol). n-Hexane was added to the resulting fraction to crystallize the product, followed by filtration to give 431 mg (yield 72.2%) of 3-[4-[3-(1H-imidazol-1-yl)propoxy]phenyl]-5-ethyl-1,2,4-oxadiazole having a melting point of 74.0°–75.5 ° C.

¹H-NMR (CDCl₃), δppm: 1.45 (3H, t, J=7.33 Hz); 2.22–2.31 (2H, m); 2.96 (2H, q, J=7.32 Hz); 3.97 (2H, t, J=5.86 Hz); 4.21 (2H, t, J=6.83 Hz); 6.93 (1H, s); 6.96 (2H, d, J=9.28 Hz); 7.07 (1H, s); 7.49 (1H, s); 8.01 (2H, d, J=8.79 Hz). IR$\nu_{KBr}$ cm⁻¹: 3100, 2955, 1610, 1565, 1220.

EXAMPLE 2

3-[4-[3-(1H-imidazol-1-yl)propoxy]phenyl]-5-trichloromethyl-1,2,4-oxadiazole

The same procedures used in Example 1 were repeated to give the title compound.

Yield: 42.5%. M.P.: 101.5°–103.0° C. (purified through a silica gel column chromatography). ¹H-NMR (CDCl₃), δppm: 2.23–2.32 (2H, m); 3.99 (2H, t, J=11.77 Hz); 4.22 (2H, t, J=13.18 Hz); 6.86 (1H, s); 6.98 (2H, d, J=8.79 Hz); 7.08 (1H, s); 7.50 (1H, s); 8.06 (2H, d, J=8.79 Hz). IR$\nu_{KBr}$ cm⁻¹: 3100, 1605, 1460, 1245.

EXAMPLE 3

3-[4-[3-(1H-imidazol-1-yl)propoxy]phenyl]-5-propyl-1,2,4-oxadiazole

The same procedures used in Example 1 were repeated to give the title compound.

Yield: 96.5%. M.P.: 57.0°–58.0 ° C. (purified through a silica gel column chromatography). ¹H-NMR (CDCl₃), δppm: 1.06 (3H, t, J=7.32 Hz); 1.84–1.97 (2H, m); 2.21–2.31 (2H, m); 2.91 (2H, t, J=7.57 Hz); 3.97 (2H, t, J=5.61 Hz); 4.21 (2H, t, J=6.59 Hz); 6.92 (1H, s); 6.96 (2H, d, J=8.79 Hz); 7.07 (1H, s); 7.49 (1H, s); 8.01 (2H, d, J=8.79 Hz). IR$\nu_{KBr}$ cm⁻¹: 1610, 1585, 1560, 1460, 1420, 1360, 1250.

EXAMPLE 4

3-[4-[3-(1H-imidazol-1-yl)propoxy]phenyl]-5-cyclo-propyl-1,2,4-oxadiazole

The same procedures used in Example 1 were repeated to give the title compound.

Yield: 76.2%. M.P.: 98.0°–100.0° C. (purified through a silica gel column chromatography). ¹H-NMR (CDCl₃), δppm: 1.20–1.34 (4H, m); 2.19–2.30 (3H, m); 3.97 (2H, t, J=5.86 Hz); 4.20 (2H, t, J=6.60 Hz); 6.94 (3H, d, J=9.04 Hz); 7.07 (1H, s); 7.49 (1H, s); 7.98 (2H, d, J=9.04 Hz). IR$\nu_{KBr}$ cm⁻¹: 1610, 1590, 1570, 1465, 1420, 1250.

EXAMPLE 5

3-[4-[3-(1H-imidazol-1-yl)propoxy]phenyl]-5-phenyl-1,2,4-oxadiazole

The same procedures used in Example 1 were repeated to give the title compound.

Yield: 67.4%. M.P.: 132.0°–133.0 ° C. (recrystallized from benzene/n-hexane) ¹H-NMR (CDCl₃), δppm: 2.22–2.31 (2H, m); 3.99 (2H, t, J=5.86 Hz); 4.21 (2H, t, J=6.84 Hz); 6.93–7.08 (4H, m); 7.50–7.64 (4H, m); 8.09–8.24 (4H, m). IR$\nu_{KBr}$ cm⁻¹: 1600, 1560, 1490, 1420, 1350, 1250.

EXAMPLE 6

3-[4-[3-(2-methyl-1H-imidazol-1-yl)propoxy]phenyl]-5-ethyl-1,2,4-oxadiazole

The same procedures used in Example 1 were repeated to give the title compound.

Yield: 92.6%. M.P.: 77.0°–78.5° C. (purified through a silica gel column chromatography). ¹H-NMR (CDCl₃), δppm: 1.44 (3H, t, J=7.57 Hz); 2.16–2.25 (2H, m); 2.36 (3H, s); 2.95 (2H, q, J=7.57 Hz); 3.96 (2H, t, J=5.62 Hz); 4.09 (2H, t, J=6.83 Hz); 6.81 (1H, d, J=1.22 Hz); 6.91 (1H, d, J=1.22 Hz); 6.96 (2H, d, J=9.03 Hz); 8.01 (2H, d, J=9.03 Hz). IRν$_{KBr}$ cm$^{-1}$: 1615, 1570, 1420, 1250, 1180, 1040.

EXAMPLE 7

3-[4-[3-(1H-benzimidazol-1-yl)propoxy]phenyl]-5-ethyl-1,2,4-oxadiazole

The same procedures used in Example 1 were repeated to give the title compound.

Yield: 84.4%. M.P.: 100.0°–101.0 ° C. (purified through a silica gel column chromatography). $^1$H-NMR (CDCl$_3$), δppm: 1.45 (3H, t, J=7.57 Hz); 2.33–2.41 (2H, m); 2.96 (2H, q, J=7.57 Hz); 3.98 (2H, t, J=5.61 Hz); 4.46 (2H, t, J=6.59 Hz); 6.96 (2H, d, J=8.79 Hz); 7.26–7.30 (2H, m); 7.41–7.44 (1H, m); 7.80–7.83 (1H, m); 7.90 (1H, s); 8.01 (2H, d, J=8.79 Hz). IRν$_{KBr}$ cm$^{31}$ $^1$: 1610, 1580, 1560, 1490, 1420, 1360, 1250, 1170, 1040.

EXAMPLE 8

3-[4-(3-diethylaminopropoxy)phenyl]-5-ethyl-1,2,4-oxadiazole

The same procedures used in Example 1 were repeated to give the title compound.

Yield: 68.2% (purified through a silica gel column chromatography). MS (m/z): 303 (M+). $^1$H-NMR (CDCl$_3$), δppm: 1.05 (6H, t, J=7.08 Hz); 1.44 (3H, t, J=7.57 Hz); 1.91–2.01 (2H, m); 2.53–2.67 (6H, m); 2.95 (2H, q, J=7.57 Hz); 4.07 (2H, t, J=6.34 Hz); 6.97 (2H, d, J=8.79 Hz); 7.99 (2H, d, J=8.79 Hz). IRν$_{NaCl}$cm$^{-1}$: 1615, 1590, 1420, 1250, 1175.

EXAMPLE 9

3-[4-(3-dipropylaminopropoxy)phenyl]-5-phenyl-1,2,4-oxadiazole

The same procedures used in Example 1 were repeated to give the title compound.

Yield: 82.4%. M.P.: 55.0°–57.0° C. (purified through a silica gel column chromatography). $^1$H-NMR (CDCl$_3$), δppm: 0.87 (6H, t, J=7.33 Hz); 1.40–1.51 (4H, m); 1.90–2.00 (2H, m); 2.37–2.64 (4H, m); 4.09 (2H, t, J=6.35 Hz); 7.01 (2H, d, J=6.84 Hz); 7.51–7.61 (3H, m); 8.10 (2H, d, J=8.78 Hz); 8.21(2H, dd, J=8.05, 1.46 Hz). IRν$_{KBr}$ cm$^{-1}$: 1600, 1560, 1490, 1415, 1360, 1250.

EXAMPLE 10

3-[4-(3-phthalimidopropoxy)phenyl]-5-ethyl-1,2,4-oxadiazole

The same procedures used in Example 1 were repeated to give the title compound.

Yield: 79.1%. M.P.: 135.0°–136.0 ° C. (recrystallized from ethanol). $^1$H-NMR (CDCl$_3$), δppm: 1.44 (3H, t, J=7.57 Hz); 2.17–2.26 (2H, m); 2.95 (2H, q, J=7.57 Hz); 3.93 (2H, t, J=6.83 Hz); 4.09 (2H, t, J=6.10 Hz); 6.86 (2H, d, J=8.79 Hz); 7.70–7.75 (2H, m); 7.81–7.86 (2H, m); 7.95 (2H, d, J=8.79 Hz). IRν$_{KBr}$ cm$^{-1}$: 1720, 1615, 1570, 1390, 1260.

EXAMPLE 11

3-[4-(3-morpholinopropoxy)phenyl]-5-ethyl-1,2,4-oxadiazole

The same procedures used in Example 1 were repeated to give the title compound.

Yield: 93.7%. M.P.: 52.0°–53.0 ° C. (purified through a silica gel column chromatography). $^1$H-NMR (CDCl$_3$), δppm: 1.44 (3H, t, J=7.57 Hz); 1.95–2.05 (2H, m); 2.46–2.57 (6H, m); 2.96 (2H, q, J=7.57 Hz); 3.73 (4H, t, J=4.64 Hz); 4.09 (2H, t, J=6.35 Hz); 6.98 (2H, d, J=8.79 Hz); 8.00 (2H, d, J=8.79 Hz). IRν$_{KBr}$$^{-1}$: 1610, 1590, 1565, 1250, 1115.

EXAMPLE 12

3-[4-(3-piperidinopropoxy)phenyl]5-ethyl-1,2,4-oxadiazole

The same procedures used in Example 1 were repeated to give the title compound.

Yield: 34.7%. M.P.: 160.0°–163.0 ° C. (purified through a silica gel column chromatography). $^1$H-NMR (CDCl$_3$), δppm: 1.44 (3H, t, J=7.57 Hz); 1.59–1.65 (4H, m); 1.98–2.08 (2H, m); 2.45–2.56 (4H, m); 2.96 (2H, q, J=7.57 Hz); 4.07 (2H, t, J=6.35 Hz); 6.97 (2H, dd, J=9.03, 2.02 Hz); 7.99 (2H, dd, J=9.03, 2.02 Hz). IRν$_{KBr}$ cm$^{-1}$: 1610, 1590, 1565, 1360, 1250, 1165.

EXAMPLE 13

3-[4-[3-(4-methylpiperazinyl)propoxy]phenyl]-5-ethyl-1,2,4-oxadiazole

The same procedures used in Example 1 were repeated to give the title compound.

Yield: 69.4%. M.P.: 55.0°–56.0° C. (purified through a silica gel column chromatography). $^1$H-NMR (CDCl$_3$), δppm: 1.44 (3H, t, J=7.56 Hz); 1.94–2.05 (2H, m); 2.30 (3H, s); 2.33–2.57 (10H, m); 2.96 (2H, q, J=7.56 Hz); 4.08 (2H, t, J=6.35 Hz); 6.97 (2H, d, J=9.03 Hz); 7.99 (2H, d, J=9.03 Hz). IRν$_{KBr}$ cm$^{-1}$: 1620, 1560, 1420, 1250.

EXAMPLE 14

3-[4-[3-(3-pyridyl)propoxy]phenyl]-5-ethyl-1,2,4-oxadiazole

The same procedures used in Example 1 were repeated to give the title compound.

Yield: 67.9%. M.P.: 63.0°–64.0 ° C. (recrystallized from benzene/n-hexane). $^1$H-NMR (CDCl$_3$), δppm: 1.44 (3H, t, J=7.57 Hz); 2.12–2.19 (2H, m); 2.85 (2H, t, J=7.33 Hz); 2.96 (2H, q, J=7.57 Hz); 4.03 (2H, t, J=6.35 Hz); 6.97 (2H, d, J=8.79 Hz); 6.99–7.26 (2H, m); 7.51–7.56 (1H, m); 8.00 (2H, d, J=8.79 Hz); 8.45–8.50 (2H,m). IRν$_{KBr}$cm$^{-1}$: 1620, 1590, 1570, 1460, 1380, 1270.

EXAMPLE 15

3-[4-(3-phenylpropoxy)phenyl]-5-ethyl-1,2,4-oxadiazole

The same procedures used in Example 1 were repeated to give the title compound.

Yield: 80.3%. M.P. 41.0°–42.0 ° C. (purified through a silica gel column chromatography). $^1$H-NMR (CDCl$_3$), δppm: 1.44 (3H, t, J=7.32 Hz); 2.08–2.18 (2H, m); 2.83 (2H, t, J=7.33 Hz); 2.95 (2H, q, J=7.32 Hz); 4.01 (2H, t, J=6.35 Hz); 6.96 (2H, d, J=8.79 Hz); 7.20–7.32 (5H, m); 7.99 (2H, d, J=8.79 Hz). IRν$_{KBr}$$^{-1}$: 2950, 1610, 1590, 1360, 1250, 1170.

EXAMPLE 16

3-(4-propoxy)phenyl-5-ethyl-1,2,4-oxadiazole

The same procedures used in Example 1 were repeated to give the title compound.

Yield: 81.3% (purified through a silica gel column chromatography). MS (m/z): 232 (M+). $^1$H-NMR (CDCl$_3$), δppm: 1.05 (3H, t, J=7.81 Hz); 1.44 (3H, t, J=7.81 Hz); 1.77–1.90 (2H, m); 2.96 (2H, q, J=7.81 Hz); 3.98 (3H, t, J=6.83 Hz); 6.97 (2H, d, J=9.27 Hz); 8.00 (2H, d, J=9.27 Hz). IRν$_{NaCl}$ cm$^{-1}$: 2950, 2925, 2860, 1610, 1585, 1565.

EXAMPLE 17

3-[4-[3-(2-oxopyrrolidin-1-yl)propoxy]phenyl]-5-phenyl-1,2,4-oxadiazole

The same procedures used in Example 1 were repeated to give the title compound.

Yield: 98.2% (purified through a silica gel column chromatography). MS (m/z): 363 (M+). $^1$H-NMR (CDCl$_3$), δppm: 1.99–2.07 (4H, m); 2.42 (2H, t, J=8.30 Hz); 3.40–3.53 (4H, m); 4.07 (2H, t, J=6.10 Hz); 7.00 (2H, d, J=8.79 Hz); 7.51–7.64 (3H, m); 8.10 (2H, d, J=8.79 Hz); 8.21 (2H, dd, J=8.30, 1.46 Hz). IRν$_{NaCl}$ cm$^{-1}$: 1610, 1590, 1250, 1165.

EXAMPLE 18

3-[4-[2-(1H-imidazol-1-yl)ethoxy]phenyl]-5-ethyl-1,2,4-oxadiazole

The same procedures used in Example 1 were repeated to give the title compound.

Yield: 89.0%. M.P: 81.0°–82.0 ° C. (purified through a silica gel column chromatography). $^1$H-NMR (CDCl$_3$), δppm: 1.44 (3H, t, J=7.57 Hz); 2.95 (2H, q, J=7.57 Hz); 4.25–4.38 (4H, m); 6.95 (2H, d, J=9.03 Hz); 7.05 (1H, d, J=1.22 Hz); 7.08 (1H, d, J=1.22 Hz); 7.61 (1H, s); 8.01 (2H, d, J=9.03 Hz). IRν$_{KBr}$ cm$^{-1}$: 1610, 1570, 1510, 1485, 1420, 1250, 1050.

EXAMPLE 19

3-(4-benzyloxy)phenyl-5-ethyl-1,2,4-oxadiazole

The same procedures used in Example 1 were repeated to give the title compound.

Yield: 48.8%. M.P.: 69.0°–70.0 ° C. (recrystallized from ethanol/n-hexane). $^1$H-NMR (CDCl$_3$), δppm: 1.44 (3H, t, J=7.81 Hz); 2.96 (2H, q, J=7.81 Hz); 5.13 (2H, s); 7.05 (2H, d, J=9.27 Hz); 7.33–7.47 (5H, m); 8.01 (2H, d, J=9.28 Hz). IRν$_{KBr}$ cm$^{-1}$: 2960, 1610, 1580, 1560, 1250.

EXAMPLE 20

3-(4-benzyloxy)phenyl-5-trichloromethyl-1,2,4-oxadiazole

The same procedures used in Example 1 were repeated to give the title compound.

Yield: 55.2%. M.P.: 107.5°–109.5° C. (recrystallized from methanol) $^1$H-NMR (CDCl$_3$), δppm: 5.41 (2H, s); 7.08 (2H, d, J=8.79 Hz); 7.32–7.47 (5H, m); 8.06 (2H, d, J=8.79 Hz). IRν$_{KBr}$cm$^{-1}$: 1610, 1565, 1465, 1420, 1250, 1170.

EXAMPLE 21

3-[4-[3-(1H-imidazol-1-yl)propoxy]phenyl]-5-trifluoromethyl-1,2,4-oxadiazole There was suspended, in 15 ml of dry pyridine, 1.302 g of 4(3-(1H-imidazol-1-yl)propoxy]benzamidoxime and 2.10 g of trifluoroacetic anhydride was dropwise added to the suspension with ice-cooling. After 30 minutes, the temperature of the reaction mixture was returned to room temperature, the mixture was stirred at this temperature for 2 hours and further heated under reflux for 18 hours. After concentration of the reaction mixture, ice water was added to the resulting residue and the mixture was basified by the addition of a 2N sodium hydroxide solution. The basic solution was extracted with chloroform, the resulting extract was washed with water and dried. After concentrating the extract, the resulting residue was purified by silica gel column chromatography (silica gel 35 g; eluent: ethanol in chloroform having a concentration gradient of 0 to 3%). The resulting product was recrystallized from benzene/n-hexane to give 1.317 g of 3-[4-[3-(1H-imidazol-1-yl)propoxy)phenyl]-5-trifluoromethyl-1,2,4-oxadiazole.

Yield: 77.9%. M.P.: 73.0°–73.5 ° C. MS (m/z): 339 (M+). $^1$H-NMR (CDCl$_3$), δppm: 2.23–2.32 (2H, m); 3.99 (2H, t, J=5.86 Hz); 4.22 (2H, t, J=6.59 Hz); 6.93 (1H, s); 6.99 (2H, d, J=8.79 Hz); 7.08 (1H, s); 7.49 (1H, s); 8.05 (2H, d, J=8.79 Hz). IRν$_{KBr}$ $^{-1}$: 1600, 1470, 1460, 1320, 1250, 1210.

EXAMPLE 22

3-[4-[3-(1H-imidazol-1-yl)propoxy]phenyl]-5-pentafluoroethyl-1,2,4-oxadiazole The same procedures used in Example 21 were-repeated to give the title compound.

Yield: 38.1%. M.P.: 60.5°–61.5 ° C. (purified through a silica gel column chromatography). MS (m/z): 388 (M+). $^1$H-NMR (CDCl$_3$), δppm: 2.23–2.32 (2H, m); 3.99 (2H, t, J=5.86 Hz); 4.22 (2H, t, J=6.59 Hz); 6.93 (1H, s); 7.00 (2H, d, J=8.79 Hz); 7.08 (1H, s); 7.49 (1H, s); 8.07 (2H, d, J=8.79 Hz). IRν$_{KBr}$ cm$^{-1}$: 1610, 1480, 1460, 1250, 1220, 1150.

EXAMPLE 23

3-[4-[3-(1H-imidazol-1-yl)propoxy]phenyl]-5-heptafluoropropyl-1,2,4-oxadiazole The same procedures used in Example 21 were repeated to give the title compound.

Yield: 70.0%. M.P.: 60.0°–60.5 ° C. (recrystallized from benzene/n-hexane). $^1$H-NMR (CDCl$_3$), δppm: 2.27–2.36 (2H, m); 4.20 (2H, t, J=5.86 Hz); 4.28 (2H, t, J=6.60 Hz); 6.97 (1H, s); 7.00 (2H, d, J=9.03 Hz); 7.12 (1H, s); 7.87 (1H, s); 8.07 (2H, d, J=9.03 Hz). IRν$_{KBr}$ cm$^{-1}$: 1610, 1590, 1250, 1165.

EXAMPLE 24

3-[4-[3-(1H-imidazol-1-yl)propoxy]phenyl]-5-methyl-1,2,4-oxadiazole

The same procedures used in Example 21 were repeated to give the title compound.

Yield: 99.0%. M.P.: 110.0°–112.5° C. (recrystallized from benzene/n-hexane). $^1$H-NMR (CDCl$_3$), δppm: 2.21–2.31 (2H, m); 2.63 (3H, s); 3.97 (2H, t, J=5.86 Hz); 4.21 (2H, t, J=6.84 Hz); 6.92–6.98 (3H, m); 7.07 (1H, s);

7.49 (1H, s); 8.00 (2H, d, J=8.79 Hz). IR$\nu_{KBr}$ cm$^{-1}$: 3100, 2955, 1610, 1565, 1420, 1345.

EXAMPLE 25

3-[4-(3-dipropylaminopropoxy)phenyl]-5-methyl-1,2,4-oxadiazole

The same procedures used in Example 21 were repeated to give the title compound.

Yield: 77.0%. $^1$H-NMR (CDCl$_3$), δppm: 0.87 (6H, t, J=7.33 Hz); 1.39–1.50 (4H, m); 1.89–1.98 (2H, m); 2.37–2.42 (4H, m); 2.61 (2H, t, J=6.84 Hz); 4.07 (2H, t, J=6.35 Hz); 6.97 (2H, d, J=9.28 Hz); 7.98 (2H, d, J=9.28 Hz). IR$\nu_{NaCl}$ cm$^{-1}$: 1610, 1570, 1480, 1420, 1350, 1250.

EXAMPLE 26

3-(4-(3-pyridylmethyloxy)phenyl]-5-methyl-1,2,4-oxadiazole

The same procedures used in Example 21 were repeated to give the title compound.

Yield: 69.4%. M.P.: 55.0°–56.0 °C. (recrystallized from ethanol). $^1$H-NMR (CDCl$_3$), δppm: 2.64 (3H, s); 5.14 (2H, s); 7.06 (2H, d, J=9.03 Hz); 7.32–7.37 (1H, m); 7.77–7.82 (1H, m); 8.02 (2H, d, J=9.03 Hz); 8.60–8.62 (1H, m); 8.71 (1H, br-s). IR$\nu_{KBr}$cm$^{-1}$: 1610, 1565, 1480, 1420, 1260.

EXAMPLE 27

3-[4-(4-pyridylmethyloxy)phenyl]-5-methyl-1,2,4-oxadiazole

The same procedures used in Example 21 were repeated to give the title compound.

Yield: 66.7%. M.P.: 132.0°–133.0 °C. (recrystallized from ethanol). $^1$H-NMR (CDCl$_3$), δppm: 2.64 (3H, s); 5.16 (2H, s); 7.05 (2H, d, J=9.03 Hz); 7.37 (2H, d, J=6.10 Hz); 8.02 (2H, d, J=9.03 Hz); 8.64 (1H, d, J=6.10 Hz). IR$\nu_{KBr}$cm$^{-1}$: 1620, 1600, 1570, 1480, 1420, 1260.

EXAMPLE 28

3-(4-propoxy)phenyl-5-methyl-1,2,4-oxadiazole

The same procedures used in Example 21 were repeated to give the title compound.

Yield: 47.7%. M.P.: 46.0°–48.0 °C. (recrystallized from benzene/n-hexane) $^1$H-NMR (CDCl$_3$), δppm: 1.05 (3H, t, J=7.33 Hz); 1.77–1.90 (2H, m); 2.63 (3H, s); 3.98 (2H, t, J=6.60 Hz); 6.97 (2H, d, J=8.80 Hz); 7.98 (2H, d, J=8.80 Hz). IR$\nu_{KBr}$ cm$^{-1}$: 2960, 2920, 1610, 1590, 1570, 1460, 1360, 1250, 1230, 1170.

EXAMPLE 29

3-[4-(3-phenylpropoxy)phenyl]-5-methyl-1,2,4-oxadiazole

The same procedures used in Example 21 were repeated to give the title compound.

Yield: 55.2%. M.P.: 78.5°–79.0 °C. (recrystallized from ethanol/n-hexane) $^1$H-NMR (CDCl$_3$), δppm: 2.11–2.18 (2H, m); 2.63 (3H, s); 2.83 (2H, t, J=7.33 Hz); 4.02 (2H, t, J=6.35 Hz); 6.96 (2H, d, J=8.79 Hz); 7.20–7.30 (5H, m); 7.98 (2H, d, J=8.79 Hz). IR$\nu_{KBr}$ cm$^{-1}$: 2950, 2900, 1610, 1595, 1250.

EXAMPLE 30

3=(4-benzyloxy)phenyl-5-methyl-1,2,4-oxadiazole

The same procedures used in Example 21 were repeated to give the title compound.

Yield: 81.4%. M.P.: 107.0°–108.0° C. (recrystallized from ethanol). $^1$H-NMR (CDCl$_3$), δppm: 2.62 (3H, s); 5.11 (2H, s); 7.05 (2H, d, J=9.28 Hz); 7.34–7.50 (5H, m); 8.00 (2H, d, J=9.28 Hz). IR$\nu_{KBr}$ cm$^{-1}$: 1610, 1595, 1255.

EXAMPLE 31

3-[4-(3-chlorobenzyloxy)phenyl]-5-methyl-1,2,4-oxadiazole

The same procedures used in Example 21 were repeated to give the title compound.

Yield: 89.3%. M.P.: 96.0°–98.0° C. (recrystallized from benzene/n-hexane). $^1$H-NMR (CDCl$_3$), δppm: 2.64 (3H, s); 5.10 (2H, s); 7.05 (2H, d, J=8.79 Hz); 7.31–7.32 (3H, m); 7.45 (1H, s); 8.01 (2H, d, J=8.79 Hz). IR$\nu_{KBr}$ cm$^{-1}$: 1610, 1590, 1250.

EXAMPLE 32

3-[4-[3-(1H-imidazol-1-yl)propoxy]phenyl]-5-methyl-amino-1,2,4-oxadiazole

To 10 ml of a 40% methylaminomethanol solution, there was added 581 mg of 3-[4-(1H-imidazol-1-yl)propoxy]phenyl]-5-trichlororomethyl-1,2,4-oxadiazole, the resulting mixture was refluxed under heating for 3 hours, followed by recrystallization of the resulting residue from ethanol to give 311 mg of 3-(4-[3-(1H-imidazol-1-yl)propoxy]phenyl]-5-methylamino-1,2,4-oxadiazole.

Yield: 72.7%. M.P.: 153.5°–155.0° C. $^1$H-NMR (CDCl$_3$), δppm: 2.23–2.27 (2H, m); 3.14 (3H, d, J=4.88 Hz); 3.97 (2H, t, J=5.86 Hz); 4.20 (2H, t, J=6.34 Hz); 5.19 (1H, br-s); 6.91 (1H, s); 6.94 (2H, d, J=8.79 Hz); 7.07 (1H, s); 7.49 (1H, s); 7.93 (2H, d, J=8.79 Hz). IR$\nu_{KBr}$ cm$^{-1}$: 1640, 1610, 1370, 1230.

EXAMPLE 33

3-(4-benzyloxyphenyl)-5-methylamino-1,2,4-oxadiazole

The same procedures used in Example 32 were repeated to give the title compound.

Yield: 90.1%. M.P.: 148.0°–149.5° C. (recrystallized from methanol). $^1$H-NMR (CDCl$_3$), δppm: 3.13 (3H, d, J=4.40 Hz); 5.12 (2H, s); 5.23 (1H, br-d, J=4.40 Hz); 7.03 (2H, d, J=8.79 Hz); 7.33–7.64 (5H, m); 7.93 (2H, d, J=8.79 Hz). IR$\nu_{KBr}$ cm$^{-1}$: 1670, 1610, 1580, 1430, 1380, 1250.

The structures of these compounds obtained in the foregoing Examples are listed in the following Tables 4 to 6.

TABLE 4

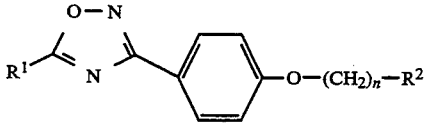

| Example No. | R$^1$ | R$^2$ |
|---|---|---|
| 1 | C$_2$H$_5$ | 3 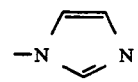 |

TABLE 4-continued $$R^1 \underset{N}{\overset{O-N}{=}} \text{—} \langle \text{phenyl} \rangle \text{—} O\text{—}(CH_2)_n\text{—}R^2$$

| Example No. | R¹ | n | R² |
|---|---|---|---|
| 2 | CCl₃ | 3 | imidazol-1-yl |
| 3 | CH₂CH₂CH₃ | 3 | imidazol-1-yl |
| 4 | cyclopropyl | 3 | imidazol-1-yl |
| 5 | C₆H₅ | 3 | imidazol-1-yl |
| 6 | C₂H₅ | 3 | 2-methylimidazol-1-yl |
| 7 | C₂H₅ | 3 | 1-methylbenzimidazol-2-yl (N-linked benzimidazole) |
| 8 | C₂H₅ | 3 | —N(C₂H₅)₂ |
| 9 | C₆H₅ | 3 | —N(CH₂CH₂CH₃)₂ |
| 10 | C₂H₅ | 3 | phthalimido |
| 11 | C₂H₅ | 3 | morpholino |

TABLE 5

| Example No. | R¹ | n | R² |
|---|---|---|---|
| 12 | C₂H₅ | 3 | piperidino |
| 13 | C₂H₅ | 3 | 4-methylpiperazin-1-yl |
| 14 | C₂H₅ | 3 | 3-pyridyl |
| 15 | C₂H₅ | 3 | C₆H₅ |
| 16 | C₂H₅ | 3 | H |
| 17 | C₆H₅ | 3 | 2-oxopyrrolidin-1-yl |
| 18 | C₂H₅ | 2 | imidazol-1-yl |
| 19 | C₂H₅ | 1 | C₆H₅ |
| 20 | CCl₃ | 1 | C₆H₅ |
| 21 | CF₃ | 3 | imidazol-1-yl |
| 22 | CF₃CF₂ | 3 | imidazol-1-yl |
| 23 | CF₃CF₂CF₂ | 3 | imidazol-1-yl |
| 24 | CH₃ | 3 | imidazol-1-yl |

TABLE 6

| Example No. | R¹ | n | R² |
|---|---|---|---|
| 25 | CH₃ | 3 | N(CH₂CH₂CH₃)₂ |
| 26 | CH₃ | 1 | 3-pyridyl |
| 27 | CH₃ | 1 | 4-pyridyl |
| 28 | CH₃ | 3 | H |
| 29 | CH₃ | 3 | C₆H₅ |
| 30 | CH₃ | 1 | C₆H₅ |
| 31 | CH₃ | 1 | 3-chlorophenyl |
| 32 | CH₃NH | 3 | imidazol-1-yl |

TABLE 6-continued

| Example No. | R¹ | | R² |
|---|---|---|---|
| 33 | CH₃NH | 1 | C₆H₅ |

The 1,2,4-oxadiazole derivatives represented by the general formula (I) according to the present invention exhibit excellent MAO-B enzyme-inhibitory activity and the inhibitory activity is quite selective for the MAO-B enzyme. Thus, the present invention can provide novel chemical substances having excellent properties suitable for treating Parkinson's disease. In addition, the compounds represented by the general formula (II) are important as intermediates for preparing the compounds of Formula (I). In other words, the compounds of Formula (I) according to the present invention can easily be prepared via the compounds of Formula (II) as intermediates.

The monoamine oxidase (MAO)-inhibitory activity of the compounds of the present invention will be explained below.

Determination of MAO-Inhibitory Activity

The MAO-inhibitory activity of the compounds of the present invention was determined according to an MAO-inhibitory activity determining method using the oxygen electrode disclosed in K. F. Tipton et al., Biochem. J., 1968,108, pp. 95-99.

A potassium phosphate buffer solution of mitochondria prepared from the liver of rats was preincubated at 37° C. with or without a compound of the present invention and then a substrate was added to the mixture to thus initiate the reaction at that temperature while the dissolved oxygen-consuming reaction due to MAO activity in the reaction solution was monitored by the oxygen electrode. In this respect, the substrates used were serotonin (5-HT) for the MAO-A activity determination and benzylamine (BA) for the MAO-B activity determination. The MAO-inhibitory activity was evaluated in terms of an IC$_{50}$ value which is the concentration of a compound tested required for reducing the rate of oxygen-consuming reaction performed in the presence of the compound to 50% of that of the reaction performed in the absence of the compound. The results obtained are listed in Table 7.

TABLE 7

| | In Vitro Inhibition of Monoamine Oxidase | | |
|---|---|---|---|
| Example No. | IC$_{50}$ (μmol/l) | | MAO-A/MAO-B |
| | MAO-A | MAO-B | |
| 1 | 200 | 0.3 | 670 |
| 2 | 200 | 0.03 | 6700 |
| 3 | 200 | 1.0 | 200 |
| 4 | 100 | 2.0 | 50 |
| 5 | 100 | 50 | 2 |
| 6 | 150 | 150 | 1 |
| 7 | 150 | 160 | 0.9 |
| 8 | 100 | 25 | 4 |
| 9 | 100 | 50 | 2 |
| 10 | 100 | 100 | 1 |
| 11 | 200 | 100 | 2 |
| 12 | 100 | 100 | 1 |
| 13 | 100 | 100 | 1 |
| 14 | 100 | 20 | 5 |
| 15 | 200 | 200 | 1 |
| 16 | 48 | 10 | 4.8 |
| 17 | 100 | 100 | 1 |
| 18 | 90 | 60 | 1.5 |
| 19 | 100 | 8 | 13 |
| 20 | 100 | 9.5 | 11 |
| 21 | 200 | 0.03 | 6700 |

TABLE 7-continued

| | In Vitro Inhibition of Monoamine Oxidase | | |
|---|---|---|---|
| Example No. | IC$_{50}$ (μmol/l) | | MAO-A/MAO-B |
| | MAO-A | MAO-B | |
| 22 | 100 | 0.09 | 1100 |
| 23 | 100 | 4.7 | 21 |
| 24 | 550 | 2.4 | 230 |
| 25 | 100 | 1 | 100 |
| 26 | 100 | 30 | 3.3 |
| 27 | 160 | 25 | 6.4 |
| 28 | 18 | 25 | 0.7 |
| 29 | 110 | 22 | 5 |
| 30 | 50 | 4.8 | 10 |
| 31 | 200 | 3 | 67 |
| 32 | 110 | 1.2 | 92 |
| 33 | 100 | 7 | 14 |
| l-Deprenil | 10 | 0.065 | 154 |

The unit dose toxicity test of the compounds of the present invention and the results obtained will be given below.

Unit Dose Toxicity Test

[1] Compounds Tested: Those prepared in Examples 2, 21 and 22.

[2] Test (i) Test Animal: ICR 5-week-old male mice.

(ii) Each test compound was suspended in a 0.5% methyl cellulose solution and then intraperitoneally administered to a group comprising 3 to 5 animals. The results obtained are summarized in the following Table 8.

TABLE 8

| Compound Tested | Dosage (mg/kg) | Surviving Rate (Surviving Animal/No. of Animal Tested) |
|---|---|---|
| Example 2 | 400 | 5/5 |
| Example 21 | 400 | 2/5 |
| Example 22 | 400 | 4/5 |

We claim:

1. A 1,2,4-oxadiazole derivative of claim 1 wherein it is a member selected from the group consisting of 3-[4-[3-(1H-imidazol-1yl)propoxy]phenyl]-5-ethyl-1,2,4-oxadiazole, 3-[4-[3-(1H-imidazol-1-yl)propoxy]phenyl]-5-trichloromethyl-1,2,4-oxadiazole, 3-[4-[3-(1H-imidazol-1-yl)propoxy]phenyl]-5-propyl-1,2,4-oxadiazole, 3-[4-[3-(1H-imidazol-1-yl)propoxy]phenyl]-5-cyclopropyl-1,2,4-oxadiazole, 3- [4-[3-(1H-imidazol-1-yl)propoxy]phenyl]-5-phenyl-1,2,4-oxadiazole, 3-[4-[3-(3-pyridyl)propoxy]phenyl]-5-ethyl-1,2,4-oxadiazole, 3-[4-[2-(1H-imidazol-1-yl)ethoxy]phenyl]-5-ethyl-1,2,4-oxadiazole, 3-(4-benzyloxy)phenyl-5-ethyl-1,2,4-oxadiazole, 3-(4-benzyloxy)phenyl-5-trichloromethyl-1,2,4-oxadiazole, 3-[4-[3-(1H-imidazol-1-yl)propoxy]phenyl]-5-trifluoromethyl-1,2,4-oxadiazole, 3-[4-[3-(1H-imidazol-1-yl)propoxy]phenyl]-5-pentafluoroethyl-1,2,4oxadiazole, 3-[4-[3-(1H-imidazol-1-yl)propoxy]phenyl]-5-heptafluoropropyl-1,2,4-oxadiazole, 3-[4-[3-(1H-imidazol-1-yl) propoxy]phenyl]-5-methyl-1,2,4-oxadiazole, 3-[4-(3pyridylmethyloxy)phenyl]-5-methyl-1,2,4-oxadiazole, 3-[4-(4pyridylmethyloxy)phenyl]-5-methyl-1,2,4-oxadiazole, 3-[4-(3phenylpropoxy)-phenyl]-5-methyl-1,2,4-oxadiazole, 3-(4-benzyloxy)phenyl]-5-methyl-1,2,4-oxadiazole, 3-[4-(3-chlorobenzyloxy)phenyl]-5-methyl-1,2,4-oxadiazole, 3-[4-[3-(1H-imidazol-1-yl)propoxy]phenyl]-5-methylamino-1,2,4-oxadiazole and 3-(4-benzyloxyphenyl)-5-methylamino-1,2,4-oxadiazole.

2. A 1,2,4-oxadiazole derivative of claim 1 wherein it is a member selected from the group consisting of 3-[4-[3-(1H-imidazol-1yl)propoxy ]phenyl]-5-ethyl-1,2,4-oxadiazole, 3-[4-[3-(1H-imidazol-1-yl)propoxy]phenyl]-5-trichloromethyl-1,2,4-oxadiazole, 3-[4-[3-(1H-imidazol-1-yl)propoxy]phenyl]-5-propyl-1,2,4-oxadiazole, 3-[4-[3-(1H-imidazol-1-yl)propoxy]phenyl]-5-cyclopropyl-1,2,4oxadiazole, 3-[4-[3-(1H-imidazol-1-yl)propoxy]phenyl]-5-phenyl]-1,2,4-oxadiazole, 3-[4-[2-(1H-imidazol-1-yl)ethoxy]phenyl]-5-ethyl-1,2,4-oxadiazole, 3-[4-[3-(1H-imidazol-1-yl)propoxy]phenyl]-5-trifluoromethyl-1,2,4-oxadiazole, 3-[4-[3-(1H-imidazol-1-yl) propoxy]phenyl]-5-pentafluoroethyl-1,2,4-oxadiazole, 3-[4-[3-(1H-imidazol-1-yl)propoxy]-phenyl]-5-heptafluoropropyl-1,2,4-oxadiazole, 3-[4-[3-(1H-imidazol-1-yl)propoxy]phenyl]-5-methyl-1,2,4-oxadiazole and 3-[4-[3-(1H-imidazol-1-yl)propoxy]-phenyl]-5-methylamino-1,2,4-oxadiazole.

3. A 1,2,4-oxadiazole derivative of claim 1 wherein it is a member selected from the group consisting of 3-[4-[3-(1H-imidazol-1yl)propoxy]phenyl]-5-ethyl-1,2,4-oxadiazole, 3-[4-[3-(1H-imidazol-1-yl)propoxy]phenyl]-5-trichloromethyl-1,2,4-oxadiazole, 3-]4-[3-(1H-imidazol-1-yl)propoxy]phenyl]-5-propyl-1,2,4-oxadiazole, 3-[4-[3-(1H-imidazol-1-yl)propoxy]phenyl]-5-trifluoromethyl-1,2,4oxadiazole, 3-[4-[3-(1H-imidazol-1-yl)propoxy]phenyl]-5-pentafluoroethyl-1,2,4-oxadiazole, 3-[4-[3-(1H-imidazol-1-yl) propoxy]-phenyl]-5-methyl-1,2,4-oxadiazole and 3-[4-[3-(1H-imidazol-1-yl)propoxy]phenyl]-5-methylamino-1,2,4-oxadiazole.

4. A 1,2,4-oxadiazole derivative of claim 1 wherein it is a member selected from the group consisting of 3-[4-[3-(1H-imidazol-1yl)propoxy]phenyl]-5-trichloromethyl-1,2,4,oxadiazol and 3-[4-[3 (1H-imidazol-1-yl)propoxy]phenyl]-5-trifluoromethyl-1,2,4-oxadiazol, 3-[4-[3-(1H-imidazol-1-yl)propoxy]phenyl]-5-pentafluoroethyl-1,2,4-oxadiazole.

5. A pharmaceutical composition containing an effective amount of a compound as set forth in claim 1 together with a pharmaceutically acceptable carrier.

6. A pharmaceutical composition containing an effective amount of a compound as set forth in claim 2 together with a pharmaceutically acceptable carrier.

7. A pharmaceutical composition containing an effective amount of a compound as set forth in claim 3 together with a pharmaceutically acceptable carrier.

8. A pharmaceutical composition containing an effective amount of a compound as set forth in claim 4 together with a pharmaceutically acceptable carrier.

9. A method of using a pharmaceutical composition containing a 1,2,4-oxadiazole derivative represented by the following formula (I) or an acid salt thereof;

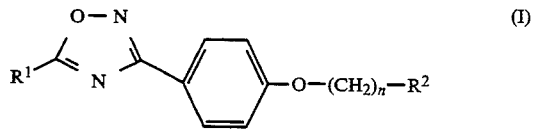

wherein $R^1$ represents a lower alkyl or cycloalkyl group, a lower alkyl group substituted with halogen atoms, a lower alkylamino group or a phenyl group; $R^2$ represents a hydrogen atom, a lower dialkylamino group, a cyclic alkylamino group, a cyclic amino group having an oxygen or nitrogen atom in the ring, a phenyl group which may be substituted with a halogen atom, a pyridyl group, an imidazolyl group, an alkyl imidazolyl group, a benzimidazolyl group or a 2-oxopyrolidinyl group; and n is 1, 2 or 3, to treat Parkinson's disease comprising administering an effective amount of said composition to a patient suffering from Parkinson's disease.

10. A method of using the pharmaceutical composition of claim 5 to treat Parkinson's disease comprising administering an effective amount of said composition to a patient suffering from Parkinson's disease.

11. A method of using the pharmaceutical composition of claim 6 to treat Parkinson's disease comprising administering an effective amount of said composition to a patient suffering from Parkinson's disease.

12. A method of using the pharmaceutical composition of claim 7 to treat Parkinson's disease comprising administering an effective amount of said composition to a patient suffering from Parkinson's disease.

13. A method of using the pharmaceutical composition of claim 8 to treat Parkinson's disease comprising administering an effective amount of said composition to a patient suffering from Parkinson's disease.

* * * * *

UNITED STATES PATENT AND TRADEMARK OFFICE
CERTIFICATE OF CORRECTION

PATENT NO. : 5,356,916
DATED : October 18, 1994
INVENTOR(S) : Hatsunori TOYOFUKU et al It is certified that error appears in the above-indentified patent and that said Letters Patent is hereby corrected as shown below:

In Column 20, line 41, delete "of claim 1 wherein it is a member".

Signed and Sealed this

Twentieth Day of June, 1995

*Attest:*

BRUCE LEHMAN

*Attesting Officer*  *Commissioner of Patents and Trademarks*